(12) United States Patent
Apel et al.

(10) Patent No.: US 7,030,079 B1
(45) Date of Patent: Apr. 18, 2006

(54) FRAGRANCE COMPOSITION EXHIBITING VARYING OLFACTIVE CHARACTERISTICS WHEN APPLIED ON DIFFERENT PERSONS

(75) Inventors: David Apel, Clifton, NJ (US); Pat Glassé, Clifton, NJ (US); Robert Hale, Clifton, NJ (US)

(73) Assignee: Fragrance Resources, Inc., Clifton, NJ (US)

( * ) Notice: Subject to any disclaimer, the term of this patent is extended or adjusted under 35 U.S.C. 154(b) by 0 days.

(21) Appl. No.: 09/611,112

(22) Filed: Jul. 6, 2000

(51) Int. Cl.
*A61K 7/46* (2006.01)

(52) U.S. Cl. .................................................. 512/1
(58) Field of Classification Search .................. 512/1
See application file for complete search history.

(56) References Cited

U.S. PATENT DOCUMENTS

| | | |
|---|---|---|
| 4,464,291 A | 8/1984 | Sprecker et al. |
| 4,545,930 A | 10/1985 | Upadek et al. |
| 5,120,709 A | 6/1992 | Cella et al. |
| 5,177,057 A * | 1/1993 | Zampino et al. .............. 512/22 |
| 5,238,915 A | 8/1993 | Fuwa et al. |
| 5,354,735 A | 10/1994 | Demole et al. |
| 5,378,468 A | 1/1995 | Suffis et al. |
| 5,380,707 A | 1/1995 | Barr et al. |
| 5,382,567 A | 1/1995 | Fuwa et al. |
| 5,554,588 A | 9/1996 | Behan et al. |
| 5,626,852 A | 5/1997 | Suffis et al. |
| 5,955,062 A | 9/1999 | McEleney et al. |
| 5,958,383 A | 9/1999 | McEleney et al. |
| 6,013,618 A | 1/2000 | Morelli et al. |

* cited by examiner

*Primary Examiner*—Monique T. Cole
(74) *Attorney, Agent, or Firm*—Manuel Valcarcel, Esq.

(57) ABSTRACT

A chemical composition that exhibits different olfactive characteristics when applied to the skin of different individuals, so as to appear to be a customized fragrance, comprising a combination of acid compounds, aromatic nitrogen containing components, aldehydes, aromatic phenols, natural essential oils containing terpenes and organic solvents suitable for skin use. When applied on the skin of different persons, the composition accents different portions of the accord to result in a marked variation of scent from person to person.

11 Claims, 11 Drawing Sheets

**Headspace Analysis:
Average Variation from the Mean Detected Quantity**
(e.g. The detected quantity of Benzaldehyde varies approximately 2.4
times more with Citric Acid than without)

FRAGRANCE COMPOSITION EXHIBITING VARYING OLFACTIVE CHARACTERISTICS WHEN APPLIED ON DIFFERENT PERSONS

BACKGROUND OF THE INVENTION

1. Field of the Invention

The present invention relates to perfume compositions. More particularly, the present invention relates to a chemical composition that exhibits different olfactive characteristics when applied to the skin of different individuals, so as to appear to be a customized fragrance.

2. Description of Related Art

Humans have applied scents and fragrances to their skin since antiquity. Originally these aesthetically pleasing materials were commonly isolated in raw form as resins, gums or essential oils from natural sources such as the bark, roots, leaves and fruit of indigenous plants. These resins, gums, and oils were directly applied to the body or diluted with water or other solvents, including in some cases, wine.

For the purposes of the present invention the terms "perfume" and "fragrance" are essentially synonymous and are used collectively or interchangeably throughout the present specification and are taken to mean the more concentrated forms of fragrance-containing compositions. Aspects of the present invention which apply to "perfumes" will therefore apply equally to "fragrances" and vice versa. Typically, colognes, eau de toilettes, after shaves, and other fragrance-containing embodiments are perfumes or fragrances which have a greater degree of dilution, usually by a volatile carrier such as ethanol.

Mixtures of fragrance materials are known by those skilled in the art of fragrances and perfumes as "accords." The term "accord" as used herein is defined as a mixture of two or more fragrance raw materials which are artfully combined to impart a pleasurable scent, odor, essence, or fragrance characteristic.

Fragrances are manufactured in varying concentrations of essential oils in alcohol and other organic solvents, designated in order of increasing concentration as eau de toilette, after shave or toilet water 2–5%; eau de cologne or cologne, 5–10%; eau de parfum or eau de perfume, 11–15%; and perfum or perfume, 16–50%. Users perceive perfume to be richer more full bodied than a less concentrated cologne and when applied to skin, perfume emits a stronger more persistent scent.

With the advent of modern chemistry, individual components responsible for the odor properties of these resins, gums and oils were isolated and subsequently characterized. Modern perfumery involves the artful compounding of fragrance materials to achieve novel fragrance compositions having defined characteristics. Many modern fragrances are no longer derived from natural sources but are synthesized by modern chemical methods as highly pure fragrance raw materials. These materials are currently formulated to produce fine perfumes, colognes, eau de toilettes, after-shave lotions, and other personal fragrance compositions. Typical components which comprise perfume fragrances are linear and cyclic alkenes (i.e., terpenes), primary, secondary and tertiary alcohols, nitrites, ethers, saturated and unsaturated aldehydes, esters, ketones, and mixtures thereof. The characteristic scent of a particular fragrance is determined by the balance of its unique mixture of components.

Those skilled in the art of preparing these fragrance-containing compositions have categorized fragrances into three types based on their relative volatility; top, middle, and base notes. For the purposes of the present invention "top note" fragrances are defined as fragrances having a high vapor pressure, and when applied to a paper sachet, vaporization takes place within 2 hours, and no scent remains; essentially, the initial impression of the perfume formulation is provided by top notes.

For the purposes of the present invention "middle note" fragrances are defined as fragrances having a medium vapor pressure, and when applied to a paper sachet, the scent remains from about 2 to about 6 hours; essentially, middle notes provide the skeleton of the perfume formulation.

For the purposes of the present invention "base note" fragrances are defined as fragrances having a low vapor pressure and high retentivity, and when applied to a paper sachet, the scent remains for more than about 6 hours; essentially, base notes provide the characteristic of the perfume formulation.

Top, middle, and base notes each serve a different purpose in the blending of fragrances and when properly formulated produce a "balanced fragrance" composition. The key to successfully formulating a fragrance-containing composition is the precise balance between these three groups of materials producing a fragrance-containing composition that diffuses during its evaporation in a manner which has an aesthetic quality.

It is recognized by those skilled in the art that descriptors which relate to aesthetic perceptions such as "top," "middle" and "base" notes are relative terms. A fragrance raw material categorized as a top note by one formulator usually has the identical classification among most other perfumers. The same is true for the middle and base notes; however, occasionally one formulator may classify a given fragrance raw material as a middle note rather than a top note, or vice versa, but this fact does not diminish the utility of a given compound or its absolute identity. Top, middle and base notes are now combined in a reproducible manner to produce perfumes, colognes, after-shave lotions, eau de toilettes, etc. for application to skin, which have unique and pleasant odor characteristics. Perfumers usually desire to produce a persistent and consistent scent in their fragrances throughout their period of evaporation.

Due to the uneven rate of evaporation of the components which comprise a fine perfume or fragrance, the initial fragrance may be quite different than the aroma perceived several hours later. This is generally perceived as a problem and is solved in many different ways by the user. One method is to "load up" on the perfume initially and rely on the natural evaporation rate to diminish the fragrance to a suitable level several hours later when the desired effect is needed. Another method which is used is to continually renew the fragrance by reapplying small amounts of the perfume to the skin at short time intervals. Neither of these solutions is adequate to overcome the diminishing level of top and middle notes over time. In fact, base notes which are present over a protracted period by virtue of their low volatility, begin to accumulate with each "re-freshing" of perfume. After some time these base notes overwhelm the other fragrance notes and destroy the original fragrance balance.

Fragrance characteristics can be varied by manipulating pH, component solubility and molecular weight, among other factors. These factors can be manipulated both in the fragrance composition and on the medium on which the fragrance is applied, e.g., human skin. The changes resulting from manipulation of these properties are often unpredictable at first. Several general characteristics can be predicted, however. Perfumes which release their fragrance materials in an acid containing medium such as the acid mantle of skin can be suitably formulated into highly alkaline matrices which typically comprise roll-on deodorants, creams, lotions, etc. Many of the fragrance ingredients which comprise perfumes, colognes, eau de toilettes, after-shave lotions, etc. are not suitable for inclusion in an alkaline pH environment; for example, many of the commonly known fragrance notes are esters and they are susceptible to hydrolysis at pH levels much above neutrality.

Human skin exhibits a "buffer capacity" which vigorously maintains a fairly constant pH value. This buffer capacity is referred to as "the acid mantle." Human skin acts rapidly to neutralize acidic or alkaline insults outside this constant pH value. This is why perfumes usually exhibit the same fragrance characteristics when applied on different individuals. Typical human skin pH ranges are from about 5 to about 7.

Nevertheless, fragrances shift in scent somewhat on application to different individuals, and olfactory discrimination varies from person to person. Balanced against subjective olfactory perception is the relative inability of most persons to discriminate precisely among scents. It is unusual, however, for one fragrance to appear to be a different fragrance when applied on different individuals. In fact, such a quality is generally perceived to be a flaw in a fragrance composition and is sought to be avoided.

Prior art efforts to manipulate fragrance properties to create new and improved fragrances have focused on improving scent consistency and longevity. For example, U.S. Pat. No. 5,380,707 to Barr et al. teaches fragrance compositions that are longer lasting and that have enhanced efficacy in that they retain the top note fragrance in a balanced manner over a relatively long period of time, in order to mask body malodor. The desired results are accomplished by including acetyl hexamethyl tetralin in the composition in an amount of 10%/–28% by weight of the overall composition.

Another example of prior art efforts to manipulate fragrance properties is disclosed in U.S. Pat. No. 6,013,618 to Morelli et al., which teaches fragrance compositions exhibiting odor longevity by controlling the release of the top, middle and base note fragrances and selecting notes that appear to blend into each other as they fade.

Still another example of prior art efforts to manipulate fragrance properties is disclosed in each of U.S. Pat. Nos. 5,238,915 and 5,382,567 to Fuwa et al., which teaches a controlled release fragrance that results when the fragrance is included in a cyclodextrine compound solution. The cyclodextrine solution's solubility, and therefore the fragrance component's inclusion ability, is changed depending on pH. A pH adjusting substance is used to manipulate fragrance release.

Still other prior art efforts to manipulate fragrance properties include: U.S. Pat. Nos. 5,378,468 and 5,626,852 to Soffis et al., which teaches a fragrancing composition having fragrancing components that are not activated until application to skin, the result achieved by manipulating the composition's pH such that fragrance is not released until the pH changes upon contact with skin; U.S. Pat. No. 5,120,709 to Cella et al., which teaches compositions and methods for enhancing the quality of applied fragrances by means of a fixative agent; and U.S. Pat. No. 4,464,291 to Specker et al., which teaches the use of norbornyl esters to enhance the aroma of perfume compositions.

As can be noted, prior art efforts have revealed many unexpected ways of manipulating fragrance properties such as strength, release rates and activation upon contact with skin. However, these prior art discoveries teach persons of skill in the fragrance art how to make fragrances consistent and definite. None of the above-described prior art items suggest or teach the opposite; i.e., formulation of fragrance compositions that exhibit markedly different olfactive characteristics when applied on different individuals.

The formulation of fragrance compositions is not always a predictable science due to the interrelationship between the structure, solubility and other properties of the materials combined in the composition. The present invention is an example of such unexpected results obtained from a novel combination of fragrance materials. The unexpected result is a fragrance that exhibits marked variation in scent when applied on different individuals, to the extent that individuals wearing the same fragrance composition of the present invention perceive it to be a different composition.

SUMMARY OF INVENTION

The present invention is a chemical composition that exhibits different olfactive characteristics when applied to the skin of different individuals, so as to appear to be a customized fragrance. The composition is preferably comprised the following classes of materials in the following quantities: (1) acid compounds at a usage level in excess of about 20.0% by weight of the overall composition; (2) aromatic nitrogen containing compounds at a usage level in excess of about 2.5% by weight of the overall composition; (3) aldehydes at a usage level in excess of about 1.0% by weight of the overall composition; (4) aromatic phenols at a usage level in excess of about 0.2% by weight of the overall composition; (5) natural essential oils containing terpenes at a usage level in excess of about 5% by weight of the overall composition; and (6) organic solvents suitable for solubility and skin use comprising the balance of the composition. The acid component appears to control the expression of different olfactory characteristics when the composition of the present invention is applied on the skin of different individuals. The acid component is preferably in excess of about 20% by weight of the overall composition. Components 2–5 can be used in varying amounts depending on the fragrance desired. The other components interact with the acid component to exhibit the varying olfactory characteristics when the accord is applied on different individuals. These components are apparently susceptible to change when taken from an acidic environment (e.g., in the bottle) to a less acidic environment (e.g., on the subject's skin). Component 6 is used to keep the accord in solution allowing for ease of use.

All of the ingredients in the formulation respond to variation in pH. The materials are kept in an activated form by the acid component. Once the materials are exposed to different skin pH and different natural skin oils the components react to result in a variation of scent when the composition is applied to the skin of different individuals by accenting different portions of the accord. The fragrance is perceivably different. It is not precisely clear whether the variation in scent occurs because of differing skin pH and/or skin oil characteristics from person to person. What is known is that the combination of components of the present invention produces the novel result of a marked variation in scent when the same fragrance is applied on different people.

The elements of preferred embodiments of the present invention are described in detail below.

DESCRIPTION OF A PREFERRED EMBODIMENT

Figure 1:
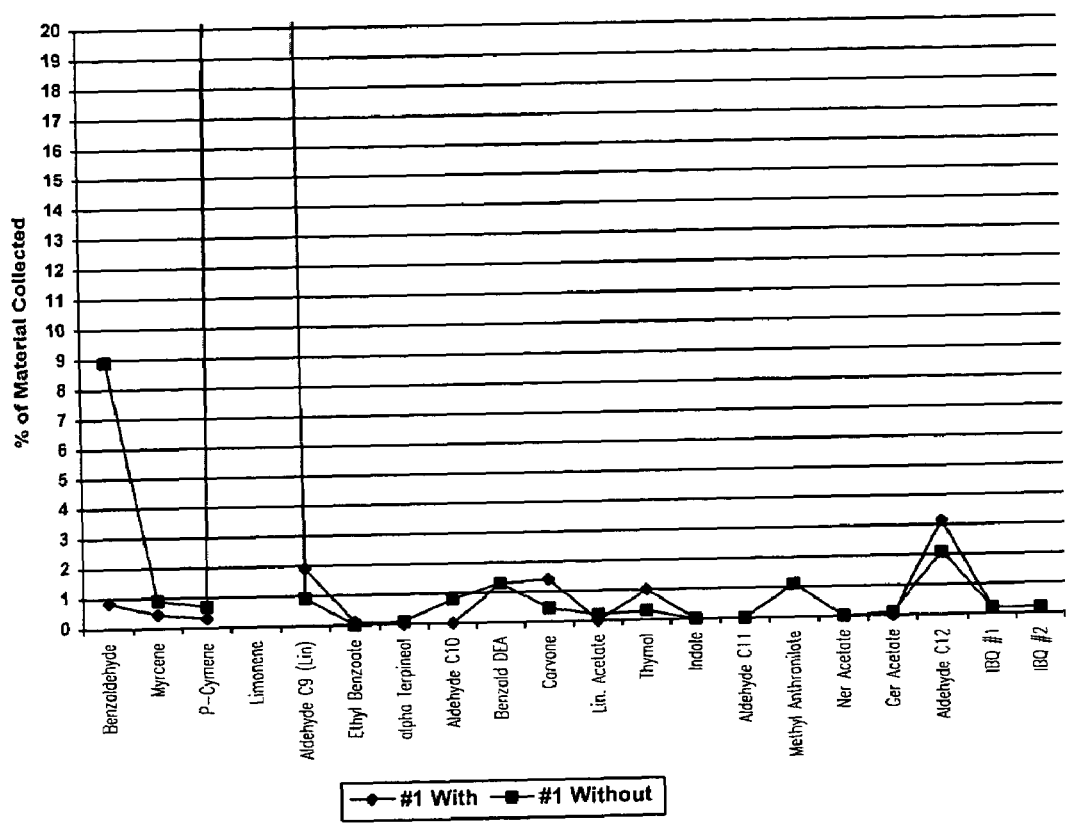
FIGS. 1–11 are graphical representations of the headspace analysis conducted with regard to application of the composition of the present invention on test subjects showing the different results obtained depending on inclusion of the acid component.

The present system invention is a chemical composition that exhibits different olfactive characteristics when applied to the skin of different individuals, so as to appear to be a customized fragrance.

The composition may contain all or some of the following classes of materials in the following quantities:

Class 1: Acid Compounds: Acid compounds are used in the composition in varying quantities, although the usage level is preferably in excess of about 20% by weight. Acid compounds used in a preferred embodiment of the invention are selected from the group consisting of alpha and beta hydroxy acids, tartaric acid, benzoic acid, citric acid, malic acid, and lactic acid.

Class 2: Aromatic Nitrogen Containing Compounds: Aromatic Nitrogen containing compounds are used in the composition preferably in excess of about 2.5% by weight, and in a preferred embodiment are selected from the group consisting of piperidine, indole, methyl anthranilate, dimethyl anthranilate, isobutyl quinoline, aromatic pyrazines and geranyl nitrile.

Class 3: Aldehydes: Aldehydes are used in the composition preferably in excess of about 1.0% by weight, and in a preferred embodiment are selected from the group consisting of hellonal, benzaldehyde, methyl benzaldehyde, lilial, lyral, aldehyde C-11, undecylenic, aldehyde C-12 lauric, triplal and geraniol oxy acetaldehyde.

Class 4: Aromatic Phenols: Aromatic phenols are used in the composition preferably in excess of about 0.2% by weight and in a preferred embodiment are selected from the group consisting of maltol, thymol, ethyl vanillin, vanillin, and isoeugenol.

Class 5: Natural Essential Oils Containing Terpenes: Natural essential oils containing terpenes are used in the composition preferably in excess of about 5% by weight and in a preferred embodiment are selected from the group consisting of D-Limonene, orange oil, lemon oil, mandarin oil, grapefruit oil, lime oil and terpineol.

Class 6: Organic Solvents Suitable for Solubility and Skin Use: Organic solvents suitable for solubility and skin use are used in the desired quantity to make up the balance of the solution with the other components in desired ratios and are in a preferred embodiment selected from the group consisting of dipropylene glycol, propylene glycol, ethyl alcohol, isopropyl myristate and mineral oil.

Components 2–5 can be used in varying amounts, depending on the fragrance desired. The organic solvent for solubility and skin use is used to create the solutions of the other components to be mixed together and the acid component, when combined with the other components, appears to control the expression of different olfactory characteristics when the composition is applied on the skin of different individuals. The acid component is preferably used in quantities in excess of about 20% by weight of the overall composition. The composition of the present invention can be formulated to itself constitute the desired end product or alternately can be mixed with other fragrance compositions to impart fragrance varying qualities.

All of the ingredients in the formulation respond to variation in pH. The composition is acidic. The materials are kept in an activated form by the acid component. Once the materials are exposed to different skin pH and different natural skin oils the components react proportionally to the individual's skin pH. The oil-soluble and water-soluble portions of the formula are additionally thought to respond differently to individual skin lipids. The result is a variation of scent among skin types when the composition is applied to skin. The custom accord responds by accenting different portions of the accord. The balance is affected thereby making some portions of the fragrance much more apparent than others. The perceived fragrance is markedly different.

Representative Formulations

Five representative formulations of compositions falling within the present invention are described below.

| Material | % W/W | | | | |
|---|---|---|---|---|---|
| | 1 | 2 | 3 | 4 | 5 |
| Citric Acid [25.0% W/W in SD 39C Alcohol] | 70.0 | 60.0 | 46.0 | 51.0 | 51.0 |
| Indole (pure FCC) [10.0% W/W in pre-blended Citric Acid @ 25.0% in SD 39C Alcohol] | 10.0 | 15.0 | 10.0 | 10.0 | 10.0 |
| Methyl Anthranilate [10.0% W/W in pre-blended Citric Acid @ 25.0% in SD 39C Alcohol] | 10.0 | 10.0 | 12.0 | 12.0 | 12.0 |
| Isobutyl Quinoline [10.0% W/W in pre-blended Citric Acid @ 25.0% in SD 39C Alcohol] | 8.0 | 10.0 | 7.0 | 3.0 | 3.0 |
| Benzaldehyde (FCC rectified) [10.0% W/W in pre-blended Citric Acid @ 25.0% in SD 39C Alcohol] | 2.0 | 5.0 | 10.0 | 10.0 | 10.0 |
| Thymol (USP) [10.0% W/W in pre-blended Citric Acid @ 25.0% in SD 39C Alcohol] | 0.0 | 0.0 | 5.0 | 2.0 | 2.0 |
| Bitter Orange Oil (Haiti) | 0.0 | 0.0 | 5.0 | 5.0 | 5.0 |
| Aldehyde C12 (Lauric FCC) [10.0% W/W in pre-blended Citric Acid @ 25.0% in SD 39C Alcohol] | 0.0 | 0.0 | 5.0 | 7.0 | 7.0 |
| Total | 100.0% | 100.0% | 100.0% | 100.0% | 100.0% |

The representative formulations generally exhibit an aldehydic-fruity-floral-earthy fragrance. The aldehydic fragrance is floral aldehydic and citrus aldehydic. The fruity fragrance is berry fruity and citrus fruity. The floral fragrance is jasmine floral and orange floral. When applied to human skin, one qualifying note from each of these categories dominates, giving many possible marked variations.

Preparation

All raw materials are preferably pre-blended in solution as designated by the brackets beside the materials. All solutions are combined and mixed thoroughly. No heat should be applied in the process. The resultant product may vary in color from water white to a deep red color.

Blind testing was conducted among a general consumer group to determine if they detected a difference in odor of representative formula #4 sprayed onto the skin of different individuals.

Test #1

Testing was conducted in groups of two people. Test subjects were each sprayed from one of two bottles. Both bottles contained the same formula #4 material, but were coded differently. Each test subject was given a questionnaire to complete without consulting the paired test subject.

Test subjects responded to the question of whether the two arms smelled the same, different or of whether they were unable to make a determination. 18 of 20 test subjects thought the formula #4 sprayed on the arms of 2 different people smelled different.

Test #2

The fragrance sample tested in this panel test was a market sample of Coty "Vanilla Fields" perfume without any added custom fragrance accord to establish a benchmark. 71.0% of the panelists thought the fragrance smelled the same on the arms of two different people. From this test it was apparent most people thought the "Vanilla Fields" did not vary from person to person.

The custom accord was then added to the "Vanilla Fields" composition to determine whether the panelists noted any differences. "Vanilla Fields" was blended with 29% representative formula #4. And the blend was then subjected to a panel test of 38 women. Multiple bottles of the same fragrance were coded differently. Test subjects were separated into groups of two or three. Each test subject was sprayed from 2 different bottles. Panelists were asked not to communicate with each other until the test was completed. Test subjects completed a questionnaire. 89% of the women tested thought the blended fragrance smelled different on the skin of their test partners as compared to themselves. The test results indicated that the custom accord #4 increases the perceived difference of a fragrance on the skin of different individuals.

Test #3

The headspace of the custom accord #4 (with citric acid) vs. custom accord #4 with citric acid removed and replaced by ethyl alcohol was analyzed by tests conducted on five individuals. "Headspace analysis" refers to gas chromatograph analysis of the fragrance materials after they are applied to skin to measure the release of such materials from the skin to the surrounding air. The pH of the test subject arm was measured by 0.04 g of custom accord #4 (with citric acid) was sprayed on the subject's arm and the sprayed area was covered with plastic film. The same amount of custom accord #4 without citric acid was sprayed on the subject's other arm and covered with plastic film. The capture was accomplished via solid phase microextraction.

The headspace analysis results were as follows:

TABLE I

| | Subject #1 | | Subject #2 | | Subject #3 | | Subject #4 | | Subject #5 | |
|---|---|---|---|---|---|---|---|---|---|---|
| pH % | M-52QR | M23NU | D52QR | D23NU | A52QR | A23NU | QR | NU | QR | NU |
| Benzaldehyde | 0.83 | 8.68 | TR | 5.34 | 8.83 | 6.38 | 2.66 | 6.29 | 1.82 | 4.69 |
| Myrcene | 0.46 | 0.89 | TR | 0.52 | 1.36 | 0.74 | 1.27 | 0.48 | 0.96 | 0.65 |
| P-Cymene | 0.25 | 0.55 | TR | 0.39 | — | 0.66 | 0.4 | 0.71 | 0.59 | 0.53 |
| Limonene | 87.26 | 80.98 | 93.38 | 86.21 | 71.01 | 89.84 | 91.88 | 88.58 | 93.08 | 91.13 |
| Aldehyde C-9/Lin | 1.92 | 0.87 | TR | TR | 0.28 | 0.41 | 0.49 | 0.16 | 0.52 | 0.10 |
| Ethyl Benzoate | 0.17 | — | TR | — | TR | — | 0.06 | — | 0.10 | — |
| α terpineol | — | 0.12 | — | 0.12 | 1.22 | — | 0.33 | 0.59 | 0.33 | 0.14 |
| Ald. C-10 | — | 0.68 | — | 0.60 | 0.55 | — | — | 0.12 | TR | TR |
| Benz. DEA | 1.42 | 1.51 | TR | 0.70 | — | 0.09 | 0.06 | TR | 0.17 | 0.09 |
| Carvone | 1.32 | 0.45 | TR | 0.53 | 2.76 | 0.32 | 1.11 | 0.37 | 1.06 | 0.28 |
| Lin Acetate | — | 0.20 | — | 0.17 | — | 0.13 | — | TR | 0.11 | 0.08 |
| Thymol | 1.10 | 0.37 | TR | 1.09 | 5.83 | 0.19 | 0.88 | 0.51 | 0.69 | 0.43 |
| Indole | — | — | — | TR | — | — | — | — | — | TR |
| Ald. C-11 | — | 0.06 | — | TR | — | TR | — | TR | TR | TR |
| Methyl Anthranilate | 1.29 | 1.21 | 6.62 | 2.22 | 4.59 | 0.44 | 0.87 | 0.97 | 0.51 | 0.93 |
| Ner. Acetate | — | — | — | 0.10 | — | 0.03 | — | TR | TR | 0.06 |
| Ald. C-12 | — | 0.12 | — | 0.26 | — | 0.20 | TR | 0.07 | 0.06 | 0.04 |
| IBQ #1 | 3.23 | 2.26 | — | 1.05 | TR | 0.43 | TR | 0.83 | TR | 0.46 |
| IBQ #2 | 0.32 | 0.24 | — | 0.29 | 0.42 | 0.09 | TR | 0.15 | TR | 0.27 |
| | 0.26 | 0.18 | — | 0.39 | — | 0.05 | — | 0.16 | TR | 0.12 |
| % Freq. In 39 C | 40.78 | 36.33 | 37.5 | 70.4 | 16.7 | 44.9 | — | — | — | — |

QR = With Citric Acid
NU = Without Citric Acid

Figure 2:
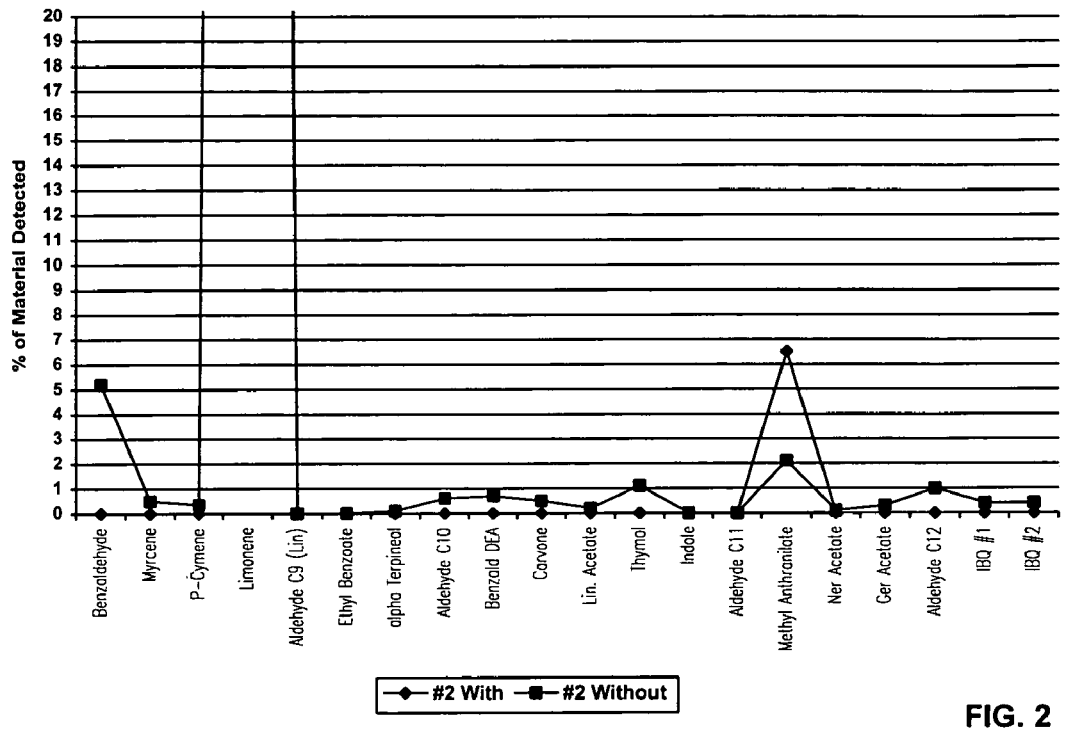
Figure 3:
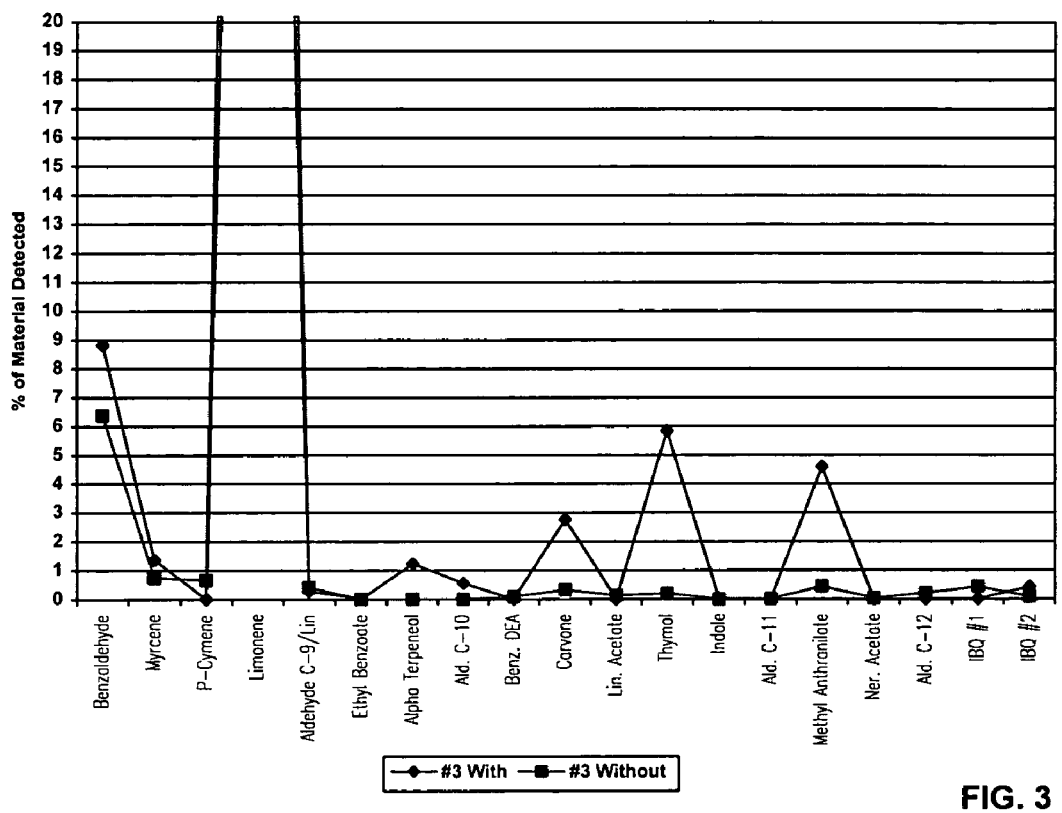
Figure 4:
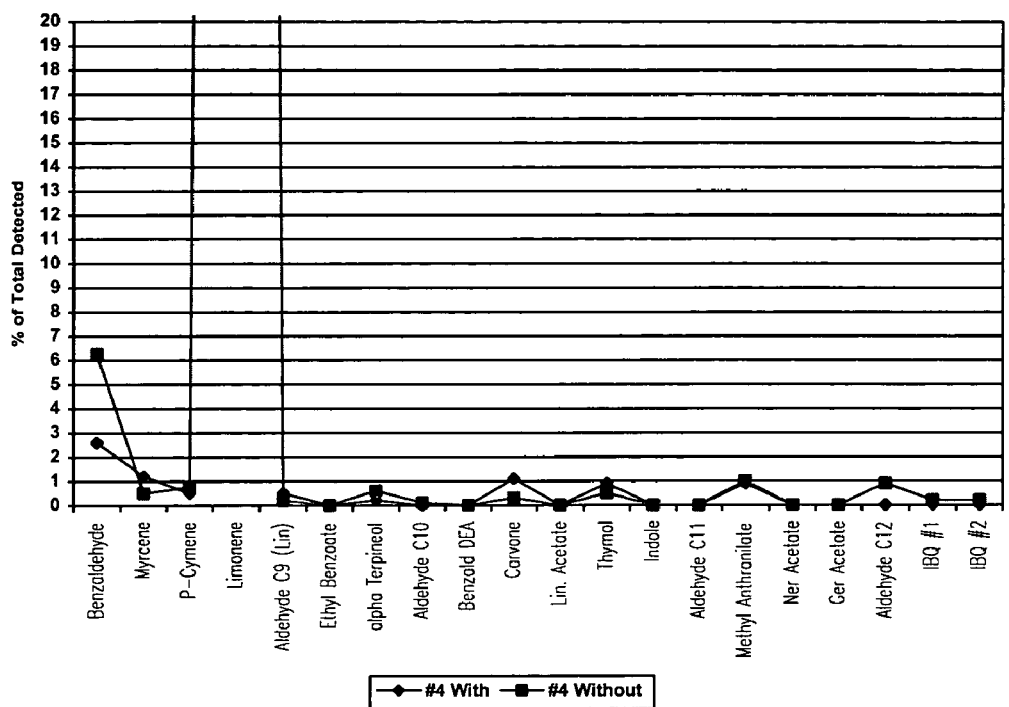
Figure 5:
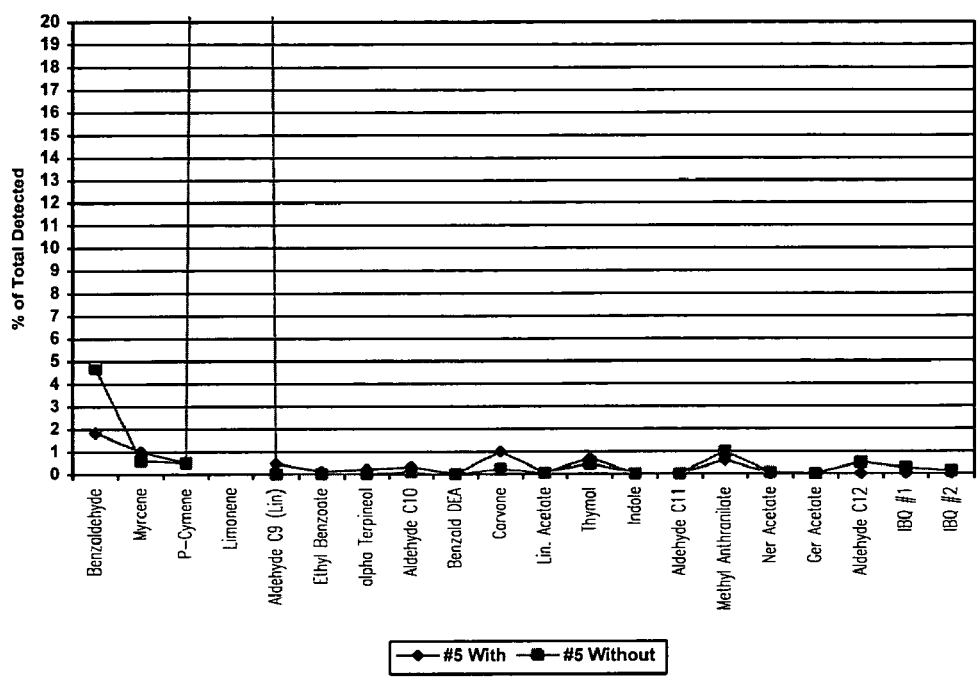
Figure 6:
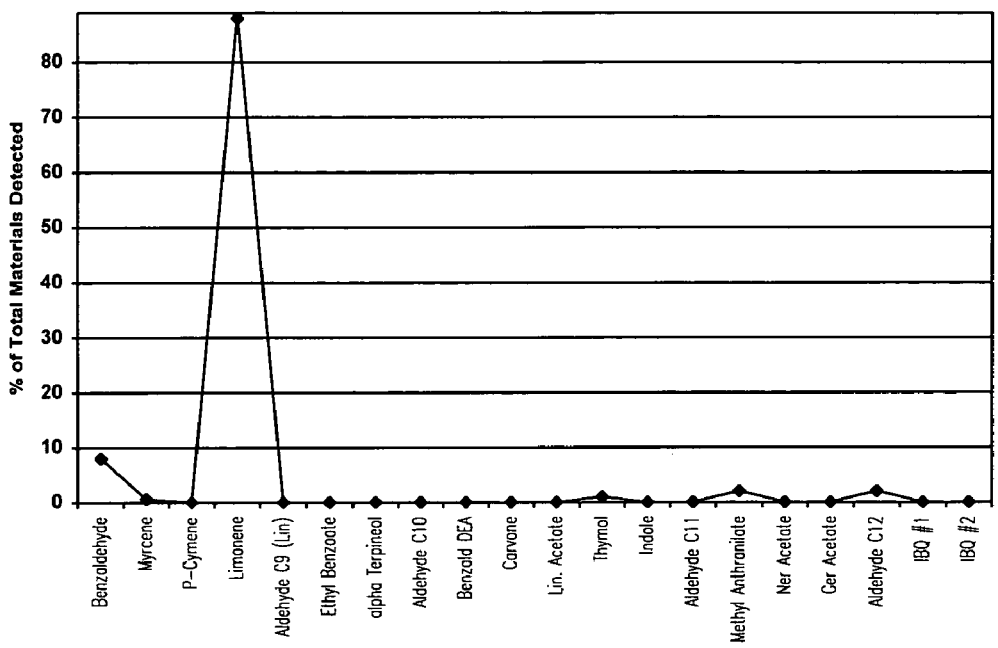
Figure 7:
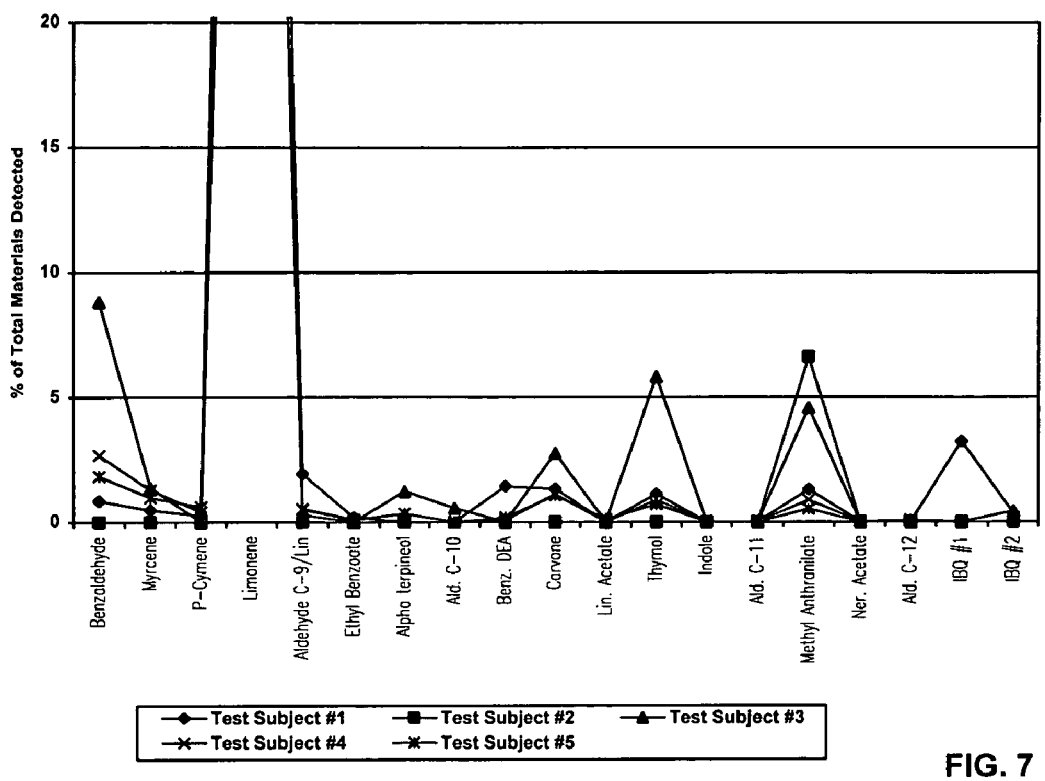
Figure 8:
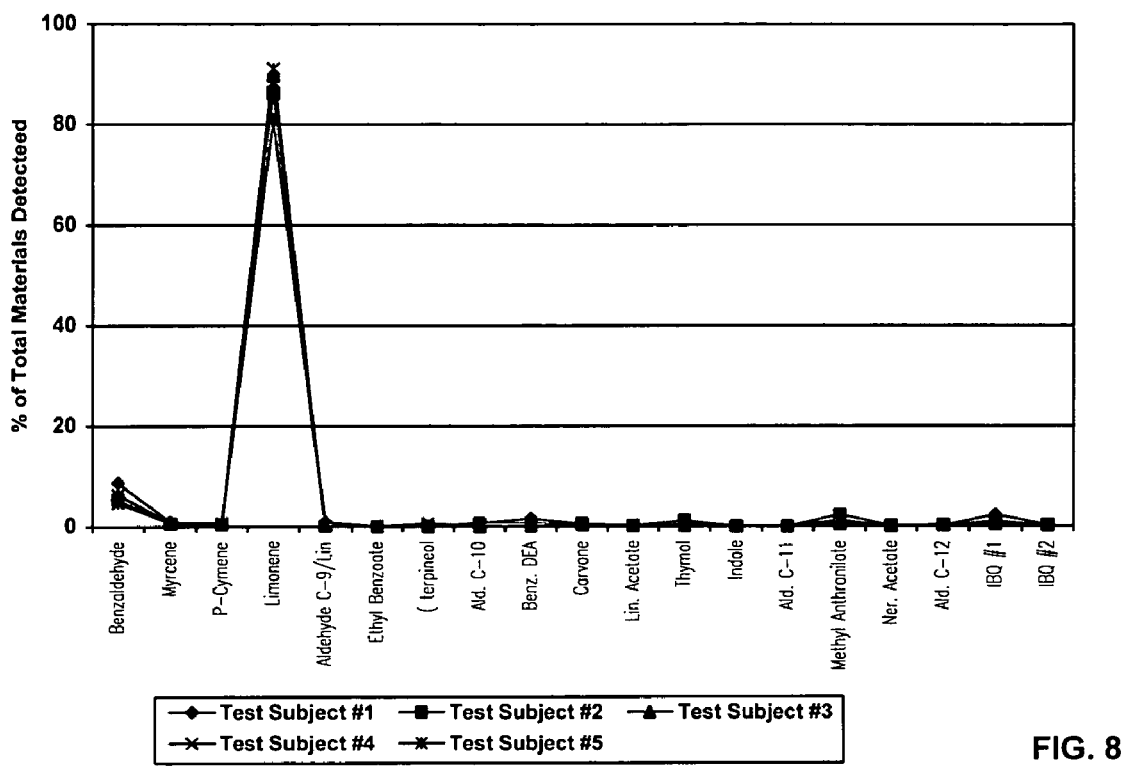
Figure 9:
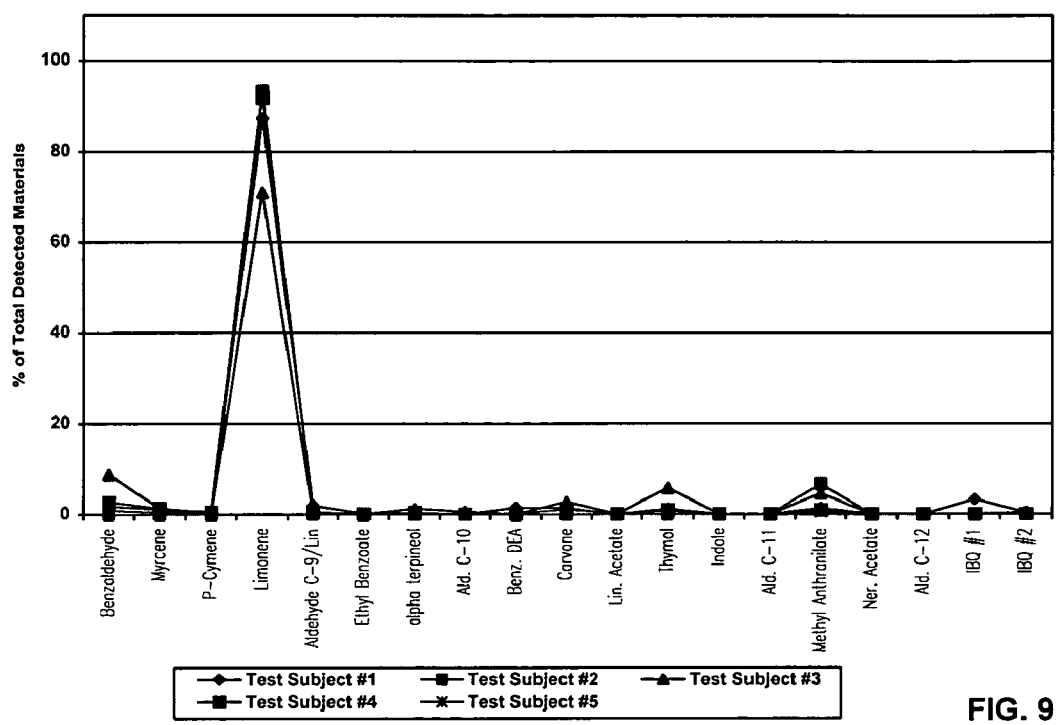
Figure 10:
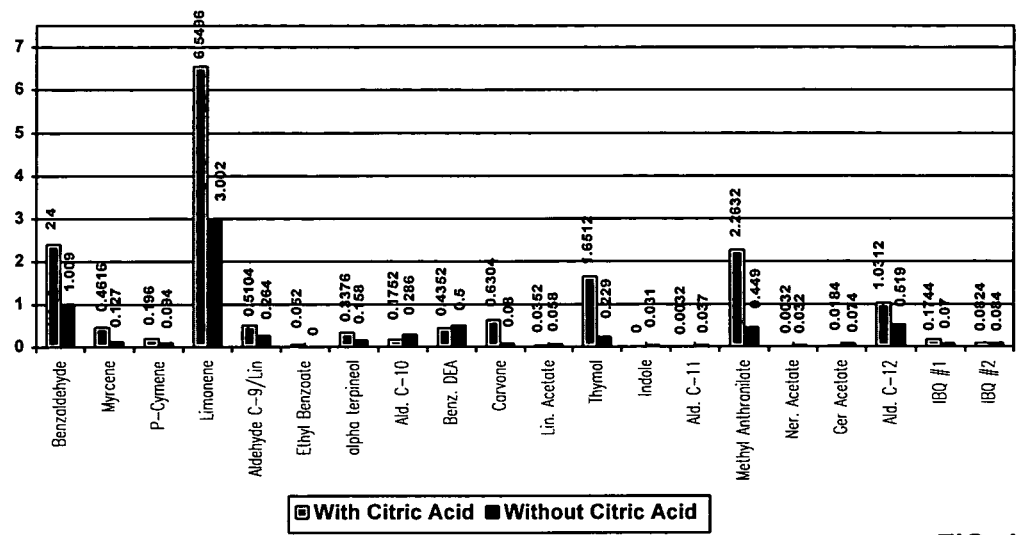
Figure 11:
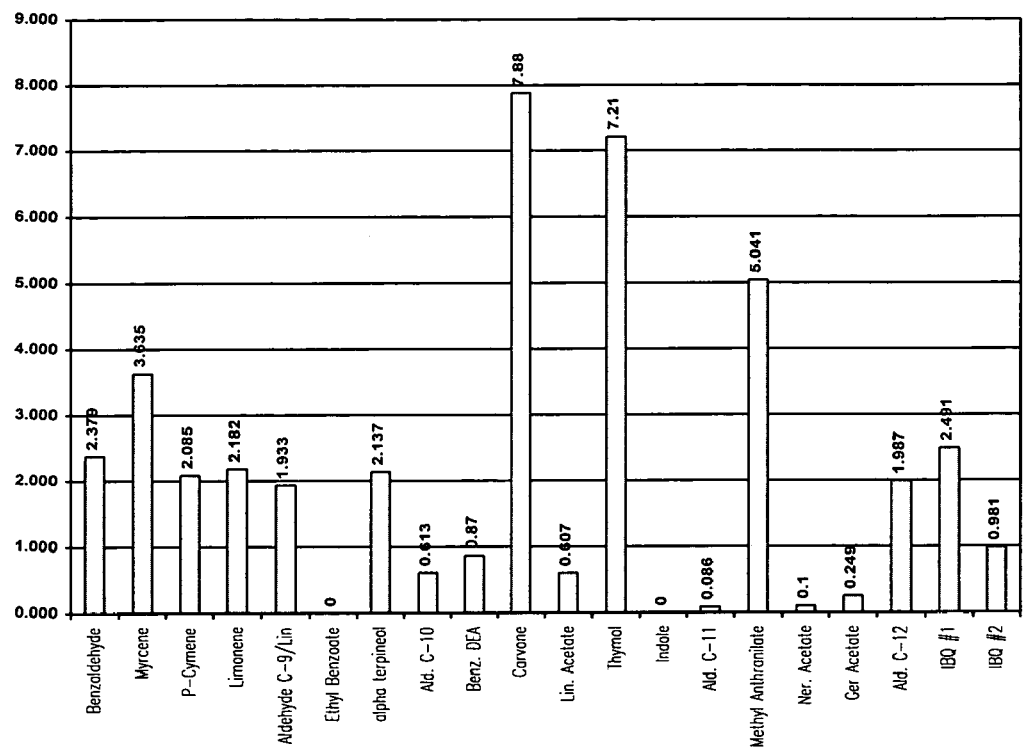

The results are presented graphically in FIGS. 1–11.

While the present invention has been shown and described herein in what is considered to be a preferred embodiment thereof, illustrating the results and advantages over the prior art obtained through the present invention, the invention is not limited to the specific embodiments described above. Thus, the forms of the invention shown and described herein are to be taken as illustrative and other embodiments may be selected without departing from the spirit and scope of the present invention.

What is claimed is:

1. A method of producing different olfactive characteristics when a fragrance composition is applied on the skin of different individuals, comprising the step of adding to said fragrance composition a combination, without application of heat, of at least about 20% by weight overall of one or more acid compounds and an effective amount of one or more compounds selected from the group consisting of aromatic nitrogen containing compounds, aldehydes, aromatic phenols and natural essential oils containing terpenes.

2. The method of claim 1, wherein said aromatic nitrogen compounds comprise at least about 2.5% by weight of overall composition.

3. The method of claim 1, wherein said aldehyde compounds comprise at least about 1.0% by weight of overall composition.

4. The method of claim 1, wherein said aromatic phenol compounds comprise at least about 0.2% by weight of the overall composition.

5. The method of claim 1, wherein said natural essential oil containing terpenes comprise at least about 5% by weight of the overall composition.

6. The method of claim 1, wherein the acid component is selected from the group consisting of alpha and beta hydroxy acids, tartaric acid, benzoic acid, citric acid, malic acid and lactic acid.

7. The method of claim 1, wherein the aromatic nitrogen containing compound component is selected from the group consisting of piperidine, indole, methyl anthranilate, dimethyl anthranilate, isobtyl quinoline, aromatic pyrazines and geramyl nitrile.

8. The method of claim 1, wherein the aldehyde component is selected from the group consisting of helional, benzaldehyde, methy benzaldehyde, lilial, lyral, aldehyde c-11 undecylenic, aldehyde c-12 lauric, triplal and geraniol oxy acetaldehyde.

9. The method of claim 1, wherein the aromatic phenol component is selected from the group consisting of maltol, thymol, ethyl vanillin, vanillin and isoeugenol.

10. The method of claim 1, wherein the natural essential oil containing terpenes component is selected from the group consisting of D-Limonene, orange oil, lemon oil, mandarin oil, grapefruit oil, lime oil, and terpineol.

11. The method of claim 1, wherein said combination further comprises an organic solvent.

* * * * *